(12) United States Patent
Benage et al.

(10) Patent No.: US 6,899,806 B2
(45) Date of Patent: May 31, 2005

(54) C-NITROSOANILINE COMPOUNDS AND THEIR BLENDS AS POLYMERIZATION INHIBITORS

(75) Inventors: Brigitte Benage, Wolcott, CT (US); Gerald J. Abruscato, Southington, CT (US); Andrew J. Eisenstein, Southbury, CT (US)

(73) Assignee: Uniroyal Chemical Company, Inc., Middlebury, CT (US)

( * ) Notice: Subject to any disclaimer, the term of this patent is extended or adjusted under 35 U.S.C. 154(b) by 14 days.

(21) Appl. No.: 10/703,592

(22) Filed: Nov. 10, 2003

(65) Prior Publication Data

US 2004/0104146 A1 Jun. 3, 2004

Related U.S. Application Data

(63) Continuation of application No. 10/030,991, filed as application No. PCT/US01/31919 on Oct. 11, 2001, now Pat. No. 6,685,823.
(60) Provisional application No. 60/240,084, filed on Oct. 16, 2000, and provisional application No. 60/240,082, filed on Oct. 16, 2000.

(51) Int. Cl.$^7$ .............................. C07C 7/20; C09K 15/16
(52) U.S. Cl. ...................... 208/48 AA; 585/950; 203/8; 252/401; 252/405; 252/407
(58) Field of Search ................ 208/48 AA; 585/950; 203/8; 252/401, 405, 407

(56) References Cited

U.S. PATENT DOCUMENTS

| | | | |
|---|---|---|---|
| 2,046,356 A | 7/1936 | Wyler et al. .................. 260/69 |
| 2,867,672 A | * 1/1959 | Hemmerich .................... 585/2 |
| 2,965,685 A | 12/1960 | Campbell ................ 260/666.5 |
| 3,163,677 A | 12/1964 | Hoffman et al. ............ 260/583 |
| 3,267,132 A | 8/1966 | Newsom et al. ......... 260/465.9 |
| 3,334,103 A | 8/1967 | Feldman et al. ............ 260/290 |
| 3,372,182 A | 3/1968 | Hoffmann et al. ........ 260/465.5 |
| 3,422,144 A | 1/1969 | Hoffmann et al. ............ 260/570 |
| 3,494,930 A | 2/1970 | Dupeyre et al. ......... 260/294.7 |
| 3,966,711 A | 6/1976 | Rasberger ................ 260/239.3 |
| 3,988,212 A | 10/1976 | Watson ............................ 203/9 |
| 4,003,800 A | 1/1977 | Bacha et al. .................... 203/9 |
| 4,040,911 A | 8/1977 | Bacha et al. .................... 203/9 |
| 4,086,147 A | 4/1978 | Watson ............................ 203/9 |
| 4,105,506 A | 8/1978 | Watson ............................ 203/9 |
| 4,132,602 A | 1/1979 | Watson ............................ 203/9 |
| 4,132,603 A | 1/1979 | Watson ............................ 203/9 |
| 4,182,658 A | 1/1980 | Watson ............................ 203/9 |
| 4,210,493 A | 7/1980 | Stewart et al. .................. 203/8 |
| 4,252,615 A | 2/1981 | Watson ............................ 203/9 |
| 4,341,600 A | 7/1982 | Watson ............................ 203/9 |
| 4,362,893 A | 12/1982 | Kurek ........................ 564/410 |
| 4,466,904 A | 8/1984 | Watson et al. .............. 252/402 |
| 4,468,343 A | 8/1984 | Butler et al. ................ 252/403 |
| 4,479,008 A | 10/1984 | Batorewicz et al. ........ 564/433 |
| 4,518,803 A | 5/1985 | Batorewicz et al. ........ 564/410 |
| 4,665,185 A | 5/1987 | Winter et al. ............... 546/184 |
| 4,774,374 A | 9/1988 | Abruscate et al. ............ 585/24 |
| 5,001,171 A | 3/1991 | Bohm et al. ................. 523/206 |
| 5,254,760 A | 10/1993 | Winter et al. .................. 585/5 |
| 5,396,004 A | 3/1995 | Arhancet et al. ............... 585/5 |
| 5,504,243 A | 4/1996 | Sakamoto et al. .......... 560/205 |
| 5,510,547 A | 4/1996 | Arhancet et al. ............... 585/5 |
| 5,545,782 A | 8/1996 | Winter et al. .................. 585/5 |
| 5,545,786 A | 8/1996 | Winter et al. ................ 585/435 |
| 5,583,247 A | 12/1996 | Nesvadba et al. ............. 560/2 |
| 5,616,774 A | 4/1997 | Evans et al. ................... 560/4 |
| 5,623,088 A | 4/1997 | Stern et al. ................. 564/112 |
| 5,648,543 A | 7/1997 | Murata et al. .............. 564/410 |
| 5,648,572 A | 7/1997 | Arhancet et al. ............... 585/5 |
| 5,648,574 A | 7/1997 | Arhancet et al. ............... 585/5 |
| 5,670,692 A | 9/1997 | Nesvadba et al. ............ 558/71 |
| 5,711,767 A | 1/1998 | Gande et al. .................. 44/423 |
| 5,739,403 A | 4/1998 | Reinartz et al. ............ 564/423 |
| 5,750,765 A | 5/1998 | Nesvadba et al. .......... 560/126 |
| 5,907,071 A | 5/1999 | Arhancet ........................ 585/5 |
| 5,910,232 A | 6/1999 | Hyde et al. ..................... 203/9 |
| 5,912,106 A | 6/1999 | Chang et al. ............. 430/281.1 |
| 5,922,244 A | 7/1999 | Koch et al. ................. 252/403 |
| 6,024,894 A | 2/2000 | Arhancet ..................... 252/404 |
| 6,054,251 A | 4/2000 | Imai et al. ................ 430/285.1 |
| 6,403,839 B1 | 6/2002 | Gracey ........................ 568/484 |
| 6,458,956 B1 | * 10/2002 | Sutoris et al. .............. 546/210 |
| 6,685,823 B2 | * 2/2004 | Benage et al. .......... 208/48 AA |

FOREIGN PATENT DOCUMENTS

| | | |
|---|---|---|
| CS | 260755 B1 | 5/1989 |
| EP | 0 178 168 A2 | 4/1986 |
| EP | 0 240 297 A1 | 10/1987 |
| EP | 0 765 856 A1 | 4/1997 |

(Continued)

OTHER PUBLICATIONS

Sidgwick, F.R.S., The Organic Chemistry of Nitrogen, 3$^{rd}$ Edition, 1966, 352–360.

(Continued)

Primary Examiner—Walter D. Griffin
(74) Attorney, Agent, or Firm—Michael P. Dilworth

(57) ABSTRACT

Disclosed herein is a method for inhibiting the premature polymerization of ethylenically unsaturated monomers comprising adding to said monomers an effective amount of:

A) at least one first inhibitor selected from the group consisting of C-nitrosoaniline compounds; and B) at least one second inhibitor selected from the group consisting of quinone alkides, nitroaromatic compounds, hydroxylamine compounds, phenylenediamine compounds, quinone compounds, and hydroquinone compounds. Also disclosed is a composition of matter comprising:

A) at least one member selected from the group consisting of C-nitrosoaniline compounds; and B) at least one member selected from the group consisting of quinone alkides, nitroaromatic compounds, hydroxylamine compounds, phenylenediamine compounds, quinone compounds, and hydroquinone compounds.

48 Claims, No Drawings

FOREIGN PATENT DOCUMENTS

| | | |
|---|---|---|
| FR | 2761060 | 9/1998 |
| GB | 1127127 | 9/1968 |
| HU | 150550 | 9/1963 |
| JP | 45017652 | 6/1970 |
| JP | 49-75541 | 7/1974 |
| JP | 49125315 | 11/1974 |
| JP | 52-133931 | 11/1977 |
| JP | 53-33578 | 3/1978 |
| JP | 62187710 | 8/1987 |
| RU | 2039757 | 7/1995 |
| SU | 202125 | 11/1967 |
| SU | 478838 | 3/1976 |
| SU | 509604 A | 8/1976 |
| SU | 334845 A1 | 1/1984 |
| WO | 97/46504 | 12/1997 |
| WO | 98/14416 | 4/1998 |
| WO | 98/25872 | 6/1998 |
| WO | 99/20584 | 4/1999 |

OTHER PUBLICATIONS

Tanczos et al., Kinetics of Radical Polymerization, Eur. Polym. J. (1982), 18(6), 487–91.

Tanczos et al., Kinetics of Radical Polymerization, Eur. Poolym. J. (1983), 19(3), 225–9.

Tanczos et al., Kinetics of Radical Copolymerization, Eur. Polym. J. (1983), 19(2), 153–7.

Georgieff, Relative Inihibitory Effect of Various Compounds on the Rate of Polymerization of Methyl Methacrylate, J. Appl. Polymer Sci, (1965), 9(6):2009–12.

Zaitsev et al., Use of Stable Free Radicals to Inhibit the Copolymeriation of Vinyl Monomers, Dopov. Akad. Nauk Ukr. RSR, Ser. B:(1977), (11), 988–91.

Georgieff, Relative Inhibitory Effect of Various Compounds on the Rate of Polymerization of Methyl Methacrylate, Journal of Applied Polymer Science. vol. 9, (1965), 2009–2018.

Boguslavaskaya, Comparative Evaluation of the Inhibiting Activity of Variou Compounds in Respect to Acrylic and Methacrylic Monome, Khimicheskaia Promyshlennost, (1967), 29–32.

Tanczos et al., Investigation of Molecule–Inhibitors in the Radicall Polymerization of Methyl Acrylate, Euro. Pol. Journal (1982), vol. 18, 295–99.

Tanczos et al., Investigation of the Effect of Molecule Inhibitors in Copolymerization, Euro. Poly. Journal (1983), 19(7), 593–95.

Kende et al., Investigation of the Effect of Nitroso Compounds on Free Radical Polymerization, Eur. Pol. Journal (1972), vol. 8, 1281–89.

Gyongyhaimi et al., Kinetics of Radical Polymerization, Eur. Poly. J. (1994), 30(12) 1457–59.

Tudos et al., Kinetics and Mechanism of Polyreactions, Int. Symp, Mecromol. Chem., Prepr., (1969) 5(25): 109–113.

Yoneda et al., Radical Polymerization of Styrene in the Presence of Aromatic Nitroso Compounds, (1970) 27(300), 269–75.

Tudos, Inhibition of Radical Copolymerization, Proc. IUPAC, I.U.P.A.C., Macromol. Symp., $28^{th}$ (1982), 90.

Laszlone et al., A gyokos polimerization kinetikaja, XVIII, Magyar Kemini Folyoirat 72. evf. (1966) 244–48.

Rabek, Katedra Technologii vol. 10, $3^{rd}$ Edition, (1965), 443–451.

Dukhnenko et al., Preparation of Low Molecular Weight Water Soluble Poly, Journal of Applied Chemistry of the USSR (1976) p. 696.

Misc. Abstracts.

* cited by examiner

C-NITROSOANILINE COMPOUNDS AND THEIR BLENDS AS POLYMERIZATION INHIBITORS

This application is a continuation of U.S. application Ser. No. 10/030,991, filed on Jan. 16, 2002, now U.S. Pat. No. 6,685,823, which is a 371 of PCT/US01/31919, filed Oct. 11, 2001, which claims the benefit of U.S. Provisional Application No. 60/240,084, filed on Oct. 16, 2000 and of U.S. Provisional Application No. 60/240,082, filed on Oct. 16, 2000.

BACKGROUND OF THE INVENTION

1. Field of the Invention

The present invention is directed to the use of at least one C-nitrosoaniline compound and/or quinone imine oxime, alone or in combination with at least one stable nitroxide free radical compound, and/or at least one nitroaromatic compound, and/or at least one quinone alkide compound, preferably a quinone methide, and/or at least one quinone compound, and/or at least one hydroquinone compound, and/or at least one hydroxylamine compound, and/or at least one phenylenediamine compound, and/or air or oxygen to inhibit the polymerization of ethylenically unsaturated monomers.

2. Description of Related Art

Many ethylenically unsaturated monomers undesirably polymerize at various stages of their manufacture, processing, handling, storage, and use. A particularly troublesome problem is equipment fouling caused by polymerization in the purification stages of the production processes of such monomers. Polymerization, such as thermal polymerization, during their purification results in the loss of the monomer and a loss in production efficiency owing to the deposition of polymer in or on the equipment being used in the purification, the deposits of which must be removed from time to time. Additionally, the formation of soluble polymer leads to loss of monomer, i.e., a lower yield, and an increase in the viscosity of any tars that may be produced. The processing of the tars then requires higher temperature and work (energy cost) to remove residual monomer.

A wide variety of compounds has been proposed and used for inhibiting uncontrolled and undesired polymerization of ethylenically unsaturated monomers. There remains a need, however, for an inhibitor that not only provides highly effective inhibition of polymerization during normal operation of a continuous manufacturing or purification process, but also provides satisfactory protection in the event of a loss of continuous inhibitor feed. While many inhibitors are known to provide sufficient protection in one of these scenarios, they have not been fully satisfactory under both normal and upset operating conditions. Accordingly, a substantial need continues in the art for improved compositions for inhibiting the polymerization of such monomers during their production and during the distillation process for purifying or separating them from impurities, as well as during transport and storage.

Aromatic nitroso and di-nitroso compounds are known to be useful as chemical agents capable of promoting the formation of filler-elastomer linkages. The aromatic nitroso compounds may be aromatic amines, including polyamines or phenolic compounds. They are also known to be useful intermediates in the production of other chemicals, such as p-aminodiphenylamine.

U.S. Pat. Nos. 3,988,212 and 4,341,600 disclose the use of N-nitrosodiphenylamine combined with dinitro-cresol derivatives for inhibiting the polymerization of vinyl aromatic compounds under vacuum distillation conditions.

U.S. Pat. No. 4,362,893 discloses that C-nitrosodiarylamines may be prepared in a single stage from diarylamines by adding alcoholic solutions of a hydrogen halide below the surface of a stirred mixture of the diphenylamine in an organic liquid containing water.

U.S. Pat. No. 4,479,008 discloses a process for preparing p-nitrosodiphenylamine hydrochloride from N-nitrosodiphenylamine and hydrogen chloride. The product is prepared in the absence of an aromatic solvent and using a solvent consisting essentially of aliphatic $C_5$–$C_{10}$ alcohol.

U.S. Pat. No. 4,518,803 discloses a process for the preparation of p-nitrosodiphenylamine hydrochloride comprising reacting diphenylamine, $C_5$–$C_{10}$ alkyl nitrite and anhydrous HCl in the presence of a $C_5$–$C_{10}$ aliphatic alcohol and essentially in the absence of an aromatic solvent.

U.S. Pat. No. 5,001,171 discloses that uncured modified rubber compositions comprising mixtures of elastomers and a reinforcing filler can be prepared by a process which comprises, inter alia, the use of at least one chemical agent capable of promoting the formation of filler-elastomer linkages. Examples of such useful chemical agents include aromatic furazan oxides, heterocyclic di-N-oxides, 1-hydroxy-benzimidazole-3-oxide compounds, 1,3-dihydroxy-benzimidazolinone compounds, and aromatic nitroso compounds.

U.S. Pat. No. 5,623,088 discloses a method of producing 4-aminodiphenylamine (4-ADPA) wherein aniline or substituted aniline derivatives and nitrobenzene are reacted under suitable conditions to produce 4-nitrodiphenylamine or substituted derivatives thereof and/or their salts, either or both of which are subsequently reduced to produce 4-ADPA or substituted derivatives thereof. The 4-ADPA or substituted derivatives thereof can be reductively alkylated to produce p-phenylenediamine products or substituted derivatives thereof which are useful as antiozonants. A second embodiment of the invention is the tetrasubstituted ammonium salts or alkyl substituted diammonium salts of 4-nitrodiphenylamine, 4-nitrosodiphenylamine and the substituted derivatives thereof wherein each substituent of the tetrasubstituted ammonium ion is independently selected from the group consisting of alkyl, aryl and arylalkyl groups and each alkyl substituent of the alkyl substituted diammonium salt is independently selected.

U.S. Pat. No. 5,648,543 discloses a process for producing a 4-nitrosodiphenylamine of the formula

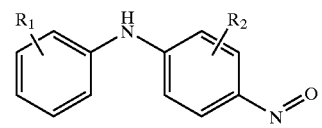

wherein $R_1$ and $R_2$ independently represent hydrogen atom, methyl group, ethyl group, cyclohexyl group, methoxy group, ethoxy group or chlorine or bromine atom, or a salt thereof, comprising treating a diphenylamine represented by the formula

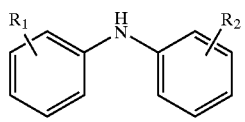

wherein $R_1$ and $R_2$ are as defined above with (i) a mixture of nitrogen oxides, (ii) a hydrogen halide and (iii) an aliphatic alcohol, wherein the atomic ratio of oxygen to nitrogen of the mixture of nitrogen oxides is more than 1.0 and less than 2.0.

U.S. Pat. No. 5,739,403 discloses the production of 4-aminodiphenylamines by reacting optionally substituted aniline with optionally substituted nitrobenzene in the presence of water and/or alcohols and organic and/or inorganic bases and then catalytically hydrogenating the resultant nitro- and/or nitrosodiphenylamine in the presence of water. The catalytic hydrogenation of the reaction mixture is performed in the presence of 25 to 80 weight percent of water, relative to the weight of the reaction mixture from the condensation reaction, the hydrogenation catalyst is removed from the hydrogenation mixture once absorption of hydrogen has ceased, 10 to 100 vol. percent of aromatic solvent, relative to the total volume of the hydrogenation mixture, is optionally added to the hydrogenation mixture, the resultant organic phase is separated in order to isolate the 4-aminodiphenylamine and the aqueous phase is returned to the initial reaction mixture.

Quinone methides, quinones, hydroquinones, hydroxylamines, and nitroxyl compounds are known polymerization inhibitors.

Quinone methides act mainly as retarders, giving a significant amount of polymer during normal inhibition usage but providing protection in the event of a plant upset during monomer purification by slowing the rate of polymer formation under static conditions. Because of the poor normal inhibition performance, quinone methides must be used in fairly high dosages, making them not very economical to use.

U.S. Pat. Nos. 4,003,800 and 4,040,911 disclose the use of quinone alkides in a styrene purification process.

The following patents, assigned to Ciba-Geigy Corporation or Ciba Specialty Chemicals Corporation, relate to quinone methides and uses thereof.

U.S. Pat. Nos. 5,583,247, 5,670,692, and 5,750,765 disclose the protection of ethylenically unsaturated monomers from premature polymerization during manufacture and storage by the incorporation therein of an effective stabilizing amount of a quinone methide compound having an electron withdrawing substituent at the 7-methylene group.

U.S. Pat. No. 5,616,774 discloses the protection of ethylenically unsaturated monomers from premature polymerization during manufacture and storage by the incorporation therein of an effective stabilizing amount of a 7-aryl quinone methide compound wherein the 7-aryl substituent is 2-, 3-, or 4-pyridyl, 2- or 3-thienyl, 2- or 3-pyrryl, 2- or 3-furyl, aryl of six to 10 carbon atoms, or said aryl substituted by one to three alkyl of one to eight carbon atoms, alkoxy of one to eight carbon atoms, alkylthio of one to eight carbon atoms, alkylamino of one to eight carbon atoms, dialkylamino of two to eight carbon atoms, alkoxycarbonyl of two to eight carbon atoms, hydroxy, nitro, amino, cyano, carboxy, aminocarbonyl, chloro, or mixtures of said substituents. The combination of these quinone methides with at least one stable nitroxyl compound is also disclosed.

U.S. Pat. No. 5,912,106 discloses a method of improving the quality and resolution of photoimages by incorporating into the photocurable resin composition to be used a selected amount of a polymerization inhibitor so that photopolymerization of the photocurable resin is inhibited in those areas not directly impinged by light. Inhibitors that can be used are selected from the group consisting of N-oxyl or nitroxide compounds, quinone methides, nitroso compounds, phenothiazine and selected phenols.

Hindered nitroxyl compounds are known to be very active inhibitors of free radical polymerizations of unsaturated monomers such as styrene, acrylic acid, methacrylic acid, and the like.

U.S. Pat. No. 3,163,677 discloses N,N,O-trisubstituted hydroxylamines and N,N-disubstituted nitroxides of the formulas:

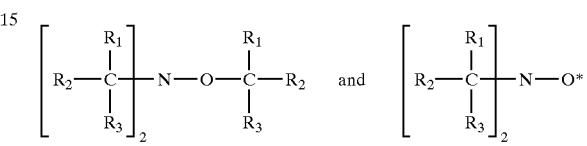

wherein $R_1$, $R_2$, and $R_3$ are each an alkyl radical having 1 to 15 carbon atoms. (As used herein, the designation N—O* denotes a stable free radical wherein the asterisk is an unpaired electron.) The N,N,O-trisubstituted hydroxylamines can be used to make the N,N-disubstituted nitroxides, which are stable free radicals and are said to be useful as polymerization inhibitors.

U.S. Pat. No. 3,267,132 discloses that the polymerization of unsaturated nitrites can be greatly inhibited by incorporating therein a minor amount of a nitroso compound selected from the group consisting of p-nitrosodiarylamines and N-nitrosoarylamines.

U.S. Pat. No. 3,334,103 discloses that nitroxides can be prepared from the corresponding heterocyclic amine wherein the nitrogen atom of the nitroxide group is attached to other than a tertiary carbon of an aliphatic group (i.e., the nitrogen atom forms a part of a heterocyclic nucleus). These nitroxides are said to have useful properties similar to those described for the N,N-disubstituted nitroxides of U.S. Pat. No. 3,163,677.

U.S. Pat. No. 3,372,182 discloses that a great variety of N,N-disubstituted, stable, free radical nitroxides not otherwise readily available can be prepared by a simple and convenient process that comprises pyrolyzing in an inert reaction medium virtually any hydroxylamine that is susceptible to cleavage of the O—C bond, e.g., tri-t-butylhydroxylamine.

U.S. Pat. No. 3,422,144 discloses stable, free radical nitroxides of the formula:

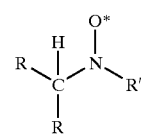

wherein R is selected from the group consisting of tertiary alkyl, aryl, alkaryl, haloaryl, carboxyaryl, alkoxyaryl, alkylthioaryl, pyridyl, and dialkylaminoaryl, and R' is tertiary alkyl. These nitroxides are said to be useful as traps for reactive free radicals both in the counting of free radicals and for inhibiting oxidation and free radical polymerization.

U.S. Pat. No. 3,494,930 discloses free radicals of the nitroxide type for use as initiators of free radical reactions, collectors of free radicals, polymerization inhibitors or antioxidants. They are constituted by nitrogenous bicyclic compounds in which one of the bridges comprises solely the nitroxide radical group and, in particular, by aza-9-bicyclo (3,3,1) nonanone-3-oxyl-9, and by aza-9-bicyclo (3,3,1) nonane oxyl-9.

U.S. Pat. No. 3,966,711 teaches that 2,2,7,7-tetraalkyl- and 2,7-dispiroalkylene-5-oxo-1,4-diazacycloheptanes substituted in the 4-position by mono- or tetravalent radicals are powerful light-stabilizers for organic polymers. They are said to possess higher compatibility than their 4-unsubstituted homologues, from which they can be synthesized by reactions known for N-alkylation. Preferred substituents in the 4-position are alkyl, alkylene, alkenyl, aralkyl, and esteralkyl groups. The 1-nitroxyls derived from the imidazolidines by oxidation with hydrogen peroxide or percarboxylic acids are also said to be good light stabilizers.

U.S. Pat. No. 4,182,658 discloses a method for preventing the polymerization of a readily polymerizable vinyl aromatic compound during distillation at elevated temperatures within a distillation apparatus that is subject to an emergency condition, such as a power outage. This method comprises force-feeding a supplemental polymerization inhibitor having a high solubility in the vinyl aromatic compound and a long duration of efficiency into each of the distillation vessels of a conventional distillation apparatus in an amount sufficient to prevent polymerization therein.

U.S. Pat. No. 4,665,185 discloses a process for the efficient preparation of nitroxyls of sterically hindered amines by the oxidation of the amine using a hydroperoxide in the presence of a small amount of a metal ion catalyst, at moderate temperature for a short period of time, to give the nitroxyl in high yield and purity.

U.S. Pat. No. 4,774,374 discloses a vinyl aromatic composition stabilized against polymerization comprising (a) a vinyl aromatic compound and (b) an effective amount of a stabilizer system in which the active ingredient consists essentially of an oxygenated species formed by the reaction of oxygen and an N-aryl-N'-alkyl-p-phenylenediamine. Also disclosed is a process for inhibiting the polymerization of vinyl aromatic compounds employing such an oxygenated species.

U.S. Pat. No. 5,254,760 teaches that the polymerization of a vinyl aromatic compound, such as styrene, is very effectively inhibited during distillation or purification by the presence of at least one stable nitroxyl compound together with at least one aromatic nitro compound.

U.S. Pat. No. 5,504,243 discloses a method for inhibiting polymerizable (meth)acrylic acid and esters thereof from polymerizing during their production, transportation and storage by using as the inhibitor N-oxyl compound and more than one compound selected from the group consisting of manganese salt compound, copper salt compound, 2,2,6,6,-tetramethylpiperidine compound and nitroso compound. The N-oxyl compound is one or more kinds selected from 2,2,6,6,-tetramethylpiperidinooxyl, 4-hydroxy-2,2,6,6,-tetramethylpiperidinooxyl and 4,4',4"-tris-(2,2,6,6,-tetramethylpiperidinooxyl)phosphite. The combined use of the inhibitors is said to provide a superior inhibiting effect to use alone.

U.S. Pat. Nos. 5,545,782 and 5,545,786 disclose that nitroxyl inhibitors in combination with some oxygen reduce the premature polymerization of vinyl aromatic monomers during the manufacturing processes for such monomers. Even small quantities of air used in combination with the nitroxyl inhibitors are said to result in vastly prolonged inhibition times for the monomers.

U.S. Pat. No. 5,711,767 discloses that the use of nitroxide compounds alone or in combination with aromatic amines, such as substituted phenylenediamines, or phenolic antioxidants provides an effective way to prevent oxidative degradation and gum formation in gasolines.

U.S. Pat. No. 5,910,232 teaches that inhibition performance in styrene processing is improved through the addition of a stable nitroxide free radical compound to the styrene feed and to the reflux of at least one column. A nontoxic retarder, such as phenylenediamine, may also optionally be added to the styrene feed and to the reflux.

U.K. Patent Number 1,127,127 discloses that acrylic acid can be stabilized against polymerization by the addition thereto of a nitroxide having the essential skeletal structure:

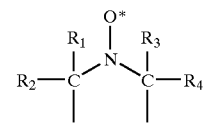

wherein $R_1$, $R_2$, $R_3$, and $R_4$ are alkyl groups and no hydrogen is bound to the remaining valencies on the carbon atoms bound to the nitrogen. The two remaining valencies that are not satisfied by $R_1$ to $R_4$ or nitrogen can also form part of a ring (e.g., 2,2,6,6 tetramethyl-4-hydroxy-piperidine-1-oxyl).

European Patent Application 0 178 168 A2 discloses a method for inhibiting the polymerization of an α,β-ethylenically unsaturated monocarboxylic acid during its recovery by distillation by using a nitroxide free radical.

European Patent Application 0 765 856 A1 discloses a stabilized acrylic acid composition in which the polymerization of the acrylic acid is inhibited during the distillation process for purifying or separating the acrylic acid as well as during transport and storage. The compositions comprise three components: (a) acrylic acid, (b) a stable nitroxyl radical, and (c) a dihetero-substituted benzene compound having at least one transferable hydrogen (e.g., a quinone derivative such as the monomethyl ether of hydroquinone (MEHQ)). During the distillation process, transport, and storage, components (b) and (c) are present in a polymerization-inhibiting amount. During the distillation process, oxygen (d) is preferably added with components (b) and (c).

WO 97/46504 concerns substance mixtures containing: (A) monomers containing vinyl groups; and (B) an active amount of a mixture which inhibits premature polymerization of the monomers containing vinyl groups during their purification or distillation and contains: (i) between 0.05 and 4.5 weight percent, relative to the total mixture (B), of at least one N-oxyl compound of a secondary amine which has no hydrogen atom at the α-C atoms; and (ii) between 99.95 and 95.5 weight percent relative to the total mixture (B), of at least one nitro compound. The publication also discloses a process for inhibiting the premature polymerization of monomers, and the use of mixture (B) for inhibiting the premature polymerization of monomers.

WO 98/14416 discloses that the polymerization of vinyl aromatic monomers such as styrene is inhibited by the addition of a composition of a stable hindered nitroxyl radical and an oxime compound.

WO 98/25872 concerns substance mixtures containing: (A) compounds containing vinyl groups; (B) an active amount of a mixture which inhibits premature polymerization of the compounds containing vinyl groups and contains: (i) at least one N-oxyl compound of a secondary amine which does not carry any hydrogen atoms on the α-carbon atoms; and (ii) at least one iron compound; (C) optionally nitro compounds; and (D) optionally co-stabilizers. The publication also discloses a process for inhibiting the premature polymerization of compounds (A) containing vinyl groups, and the use of (B) optionally mixed with nitro compounds (C) and/or co-stabilizers (D) for inhibiting the premature polymerization of radically polymerizable compounds and stabilizing organic materials against the harmful effect of radicals.

WO 99/20584 discloses that polymerization can be inhibited during the anaerobic production of styrene through the addition of a combination of a stable nitroxide free radical compound and a nontoxic phenylenediamine compound.

CS-260755 B1 is directed to the preparation of 4-substituted-2,2,6,6-tetramethylpiperidine nitroxyls as olefin stabilizers.

Hung. 150,550 discloses that free radical polymerization was inhibited with organic nitroso compounds, e.g., p-H$_2$NC$_6$H$_4$NO (I), α-nitroso-β-naphthol, or β-nitroso-α-naphthol. For example, addition of 0.3 grams of (I) to one liter of styrene is said to have resulted in the stability of the latter for months. Also, (I) could be removed with azodiisobutyronitrile.

SU-334845 A1 is directed to the inhibition of the radical polymerization of oligoester acrylates using iminoxyl radical inhibitors of a given formula.

SU-478838 is directed to the inhibition of the radical polymerization of oligoester acrylates and the prevention of oligomeric peroxides using a binary polymerization inhibitor comprising quinone.

FR 2,761,060 relates to the prevention of premature polymerization of styrene during its production by dehydrogenation of ethylbenzene by injecting into the process effluent a radical inhibitor based on an oxyl-tetramethylpiperidine derivative.

U.S. Pat. No. 4,086,147 discloses a process using 2-nitro-p-cresol as a polymerization inhibitor.

U.S. Pat. Nos. 4,105,506 and 4,252,615 disclose a process using 2,6-dinitro-p-cresol as a polymerization inhibitor.

U.S. Pat. Nos. 4,132,602 and 4,132,603 disclose the use of a halogenated aromatic nitro compound as a polymerization inhibitor for use during the distillation of vinyl aromatic compounds.

U.S. Pat. No. 4,466,904 discloses the use of phenothiazine, 4-tert-butylcatechol and 2,6-dinitro-p-cresol as a polymerization inhibitor system in the presence of oxygen during heating of vinyl aromatic compounds.

U.S. Pat. No. 4,468,343 discloses a composition and a process for utilizing 2,6-dinitro-p-cresol and either a phenylenediamine or 4-tert-butylcatechol in the presence of oxygen to prevent the polymerization of vinyl aromatic compounds during heating.

European patent application 240,297 A1 teaches the use of a substituted hydroxylamine and a dinitrophenol to inhibit the polymerization of a vinyl aromatic compound at elevated temperatures in a distillation process.

Georgieff, K. K., *J. Appl. Polymer Sci.* 9(6):2009–18 (1965) measured the inhibitory effect of the following compounds on the bulk polymerization of methyl methacrylate: hydroquinone, p-tert-butylcatechol, p-methoxyphenol, 2,4-dichloro-6-nitrophenol, n-propyl gallate, di-tert-butyl-p-cresol, 2,2'-methylenebis(4-methyl-6-tert-butylpbenol), 1-amino-7-naphthol, p-benzoquinone, 2,6-dichloro-p-benzoquinone, 2-amino-1,4-naphthoquinone, three aminoanthraquinones, diphenylamine, p-nitrosodimethylaniline, α- and β-naphthylamine, phenothiazine, N-nitroso-dimethylamine, hexamethylphosphoramide, n-dodecyl mercaptan, benzenethiol, 2,2-diphenyl-1-picrylhydrazyl, phenyl hydrazine, divinylacetylene, and various antimony and copper salts. Polymerization was carried out in a test tube in a bath at 101.2° C., benzoyl peroxide being used as initiator. Generally, phenols and naphthols were the strongest inhibitors, followed by quinones, aromatic amines, 2,2-diphenyl-1-picrylhydrazyl, antimony pentachloride, phenyl hydrazine, divinylacetylene, and the thiols.

Additionally, see also:

JP 62187710 (1987) which includes a C-nitrosoaniline derivative as a polymerization inhibitor of acrylamides at 100° C.;

JP 58014424 (1983) which includes a C-nitrosoaniline derivative as a polymerization inhibitor of aqueous solutions of acrylate esters;

JP 45017652 (1970) which includes a C-nitrosoaniline derivative as a polymerization inhibitor of aqueous solution of acrolein or methacrolein;

JP 49125315 (1974) which includes C-nitrosodiphenylamine as a polymerization inhibitor of methacrylate and acrylate esters;

JP 53-33578 (1978) which includes C-nitrosodiphenylamine as a polymerization inhibitor; and Boguslavskaya, L. S., *Khim. Prom-st.* 43(10):749–52 (1967).

Several articles have described the use of C-nitrosoaniline derivatives as inhibitors of AIBN- or benzoylperoxy-initiated polymerizations of styrene, methylacrylate, methyl methacrylate, acetonitrile, and their copolymers, e.g., Tudos, F. et. al., *Eur. Polym. J.*, 18(4):295–9(1982);
Ibid., 19(7):593–5 (1983);
Ibid., 8(11):1281–9 (1972);
Ibid., 30(12):1457–9 (1994);
Ibid., 19(3):225–9 (1983);
Ibid., 19(2):153–7 (1983);
Ibid., 18(6):487–91 (1982);
Tudos, F., *Proc. IUPAC Macromol. Symp.*, 28$^{th}$, 90 (1982);
Tudos, F. et. al., *Kinet. Mech. Polyreactions, Int. Symp. Macromol. Chem., Prepr.*, 5(25):109–113 (1969);
Yoneda, A. et al., *Kobunshi Kagaku*, 27(300):269–75 (1970); and
Zaitsev, Y. S. et al., *Dopov, Akad. Nauk Ukr. RSR, Ser. B: Geol., Khim. Biol. Nauki*, (11):988–91 (1977).

The foregoing are incorporated herein by reference in their entirety.

SUMMARY OF THE INVENTION

N-nitroso compounds and C-nitrosophenols are known as polymerization inhibitors, especially under the conditions for monomer production and processing. It has now been discovered that C-nitrosoaniline compounds are very effective polymerization inhibitors as well. Additionally, these compounds can be used in conjunction with nitroxyls, nitroaromatics, quinone methides, quinones, hydroxylamines, hydroquinones, phenylenediamines, air, or combinations thereof (hereinafter referred to as "additional compounds") to provide an enhanced inhibitor product for use during processing of unsaturated monomers, especially styrene and acrylates.

More particularly, the present invention is directed to a method for inhibiting the premature polymerization of ethylenically unsaturated monomers comprising adding to said monomers an effective amount of at least one inhibitor selected from the group consisting of C-nitrosoaniline and quinone imine oxime compounds.

In another aspect, the present invention relates to a method for distilling a feed comprising at least one polymerizable ethylenically unsaturated monomer, said method comprising the steps of:

introducing a feed comprising at least one polymerizable ethylenically unsaturated monomer into a distillation apparatus;

introducing a polymerization inhibiting effective amount of at least one inhibitor selected from the group consisting of C-nitrosoaniline and quinone imine oxime compounds into said distillation apparatus; and distilling said feed under distillation conditions in the presence of said inhibitor to recover from said distillation apparatus an overhead product of high purity ethylenically unsaturated monomer and a residual bottoms fraction having a reduced content of polymeric material. In accordance with a further embodiment, the residual bottoms fraction is recycled back into said distillation apparatus to reuse unspent inhibitor.

In another aspect, the present invention is directed to a composition of matter comprising:

A) at least one inhibitor selected from the group consisting of C-nitrosoaniline and quinone imine oxide compounds; and B) at least one inhibitor selected from the group consisting of quinone alkides, nitroxyl compounds, nitroaromatic compounds, hydroxylamine compounds, phenylenediamine compounds, quinone compounds, and hydroquinone compounds.

In another aspect, the present invention is directed to a composition of matter comprising:

A) an ethylenically unsaturated monomer and

B) an effective inhibiting amount, sufficient to prevent premature polymerization during distillation or purification of said ethylenically unsaturated monomer, of at least one inhibitor selected from the group consisting of C-nitrosoaniline and quinone imine oxime compounds used together with an effective amount of oxygen or air to enhance the inhibiting activity of said inhibitor.

DESCRIPTION OF THE PREFERRED EMBODIMENTS

The C-nitrosoaniline compounds can be prepared by C-nitrosation of the corresponding anilines in any typical manner used for the C-nitrosation of aromatic amines. For example, reaction of the amine with cold nitrous acid produces an N-nitroso compound that rearranges to a para-nitrosoaniline under the influence of an excess of hydrochloric acid. In some cases, it is more convenient to effect the nitrosation and rearrangement in one step by conducting the reaction in methanol solution in the presence of an excess of hydrogen chloride under anhydrous conditions. This procedure is described in U.S. Pat. No. 2,046,356.

Those skilled in the art will be aware that nitrosoaniline derivatives are understood to tautomerize to quinone imine oxime derivatives, i.e.,

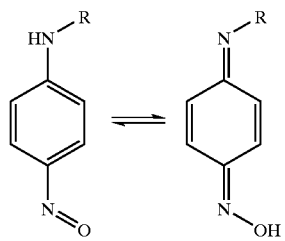

See, for example, Sidgwick, N. V., *The Organic Chemistry of Nitrogen*, Third Edition, Clarendon Press, Oxford, 1966.

Thus, both forms can be present, especially in solution at elevated temperatures, and can be expected to contribute to the inhibiting activity of these compounds. Furthermore, the quinone imine oxime tautomeric form can be enhanced by alkylation or acylation at the oxygen of the oxime. Thus, these quinone imine oxime forms and their derivatives are embodied in the present invention.

The nitrosoaniline and quinone imine oxime inhibitors of the present invention can be used alone or in combination with at least one nitroxyl compound, at least one nitroaromatic compound, at least one quinone alkide, at least one quinone derivative, at least one hydroquinone derivative, at least one hydroxylamine compound, at least one phenylenediamine compound, air or oxygen, or a mixture of the foregoing. These inhibitors are suitable for use over a wide range of temperatures, but distillation temperatures employed with the ethylenically unsaturated monomers that are stabilized by the process of the present invention typically range from about 60° C. to about 180° C., preferably from about 70° C. to about 165° C. and, more preferably, from about 80° C. to about 150° C. Such distillations are generally performed at an absolute pressure in the range of about 10 to about 1,200 mm of Hg.

The nitrosoanilines employed in the practice of the present invention are preferably of the structure:

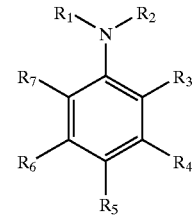

wherein $R_1$ and $R_2$ are independently selected from the group consisting of hydrogen, alkyl, aryl, acyl, hydroxyl, alkoxy, nitroso, and sulfonyl, or $R_1$ and $R_2$ can form a cyclic ring that is aryl, cycloalkyl, polyaryl, or heterocyclic;

$R_3$ through $R_7$ are independently selected from the group consisting of hydrogen, alkyl, aryl, acyl, hydroxyl, alkoxy, acyloxy, $NR_8(R_9)$, nitro, nitroso, halogen, and sulfonyl, or any two adjacent R's can form a cyclic ring that is aryl, cycloalkyl, polyaryl, or heterocyclic, provided that at least one of $R_3$ through $R_7$ must be a nitroso group; and $R_8$ and $R_9$ are independently selected from the group consisting of hydrogen, alkyl, aryl, acyl, and nitroso. Preferably $R_8$ is hydrogen and $R_9$ is alkyl.

The quinone imine oximes employed in the practice of the present invention are preferably of the structure:

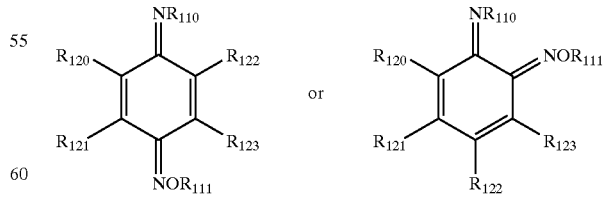

wherein $R_{120}$, $R_{121}$, $R_{122}$, and $R_{123}$ are independently selected from the group consisting of hydrogen, alkyl, aryl, cycloalkyl, heterocyclic, substituted alkyl, substituted aryl, $OR_{110}$, $NR_{110}R_{111}$, $SR_{110}$, NO, $NO_2$, CN, $COR_{112}$, and halogen, or $R_{120}$ and $R_{121}$ can be taken together and/or $R_{122}$ and $R_{123}$ can be taken together to form one or two ring structures, respectively, either of which can be of five to seven members;

$R_{110}$ and $R_{111}$ are independently selected from the group consisting of hydrogen, alkyl, aryl, acyl, benzyl, cyclic, heterocyclic, substituted alkyl or aryl where the substituents are C, O, N, S, or P, and $COR_{102}$, or $R_{110}$ and $R_{111}$ can be taken together to form a ring structure of five to seven members;

$R_{112}$ is $R_{102}$, $OR_{102}$, or $NR_{102}R_{103}$; and $R_{102}$ and $R_{103}$ are independently selected from the group consisting of hydrogen, alkyl, aryl, benzyl, cyclic, heterocyclic, and substituted alkyl or aryl where the substituents are C, O, N, S, or P, or $R_{102}$ and $R_{103}$ can be taken together to form a ring structure of five to seven members.

The nitroxyl compounds that can be employed in combination with the nitrosoanilines and quinone imine oximes in the practice of the present invention are preferably of the structure:

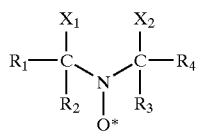

wherein $R_1$ and $R_4$ are independently selected from the group consisting of hydrogen, alkyl, and heteroatom-substituted alkyl and $R_2$ and $R_3$ are (1) independently selected from the group consisting of alkyl and heteroatom-substituted alkyl, or (2) taken together, form a ring structure with the nitrogen; and $X_1$ and $X_2$ (1) are independently selected from the group consisting of halogen, phosphorus (in any of its oxidation states), cyano, $COOR_7$, —S—$COR_7$, —$OCOR_7$, (wherein $R_7$ is alkyl or aryl), amido, —S—$C_6H_5$, carbonyl, alkenyl, or alkyl of 1 to 15 carbon atoms, or (2) taken together, form a ring structure with the nitrogen.

In a particularly preferred embodiment, the nitroxyl compound has the structural formula:

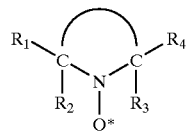

wherein $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl, and the

portion represents the atoms necessary to form a five-, six-, or seven-membered heterocyclic ring.

The quinone alkide compounds that can be employed in combination with the nitrosoanilines and quinone imine oximes in the practice of the present invention are preferably of the structure:

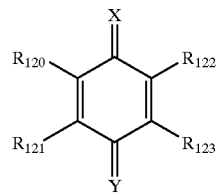

wherein

X is oxygen;

Y is $CR_{124}R_{125}$;

$R_{120}$, $R_{121}$, $R_{122}$, and $R_{123}$ are independently selected from the group consisting of hydrogen, alkyl, aryl, cycloalkyl, sulfonyl, heterocyclic, substituted alkyl, substituted aryl, $OR_{110}$, $NR_{110}R_{111}$, $SR_{110}$, NO, $NO_2$, CN, $COR_{112}$, and halogen, or $R_{120}$ and $R_{121}$ can be taken together and/or $R_{122}$ and $R_{123}$ can be taken together to form one or two ring structures, respectively, either of which can be of five to seven members;

$R_{124}$ and $R_{125}$ are independently selected from the group consisting of hydrogen, alkyl, aryl, cycloalkyl, heterocyclic, substituted alkyl, substituted aryl, $OR_{110}$, $NR_{110}R_{111}$, $SR_{110}$, $NO_2$, NO, CN, $COR_{112}$, halogen, and/or can be taken together to form a ring structure of five to seven members;

$R_{110}$ and $R_{111}$ are independently selected from the group consisting of hydrogen, alkyl, aryl, acyl, benzyl, cyclic, heterocyclic, substituted alkyl or aryl where the substituents are C, O, N, S, or P, and $COR_{102}$, or $R_{110}$ and $R_{111}$ can be taken together to form a ring structure of five to seven members;

$R_{112}$ is $R_{102}$, $OR_{102}$, or $NR_{102}R_{103}$; and $R_{102}$ and $R_{103}$ are independently selected from the group consisting of hydrogen, alkyl, aryl, benzyl, cyclic, heterocyclic, and substituted alkyl or aryl where the substituents are C, O, N, S, or P, or $R_{102}$ and $R_{103}$ can be taken together to form a ring structure of five to seven members.

The nitroaromatic compounds that can be employed in combination with the nitrosoanilines and quinone imine oximes in the practice of the present invention are preferably of the structure:

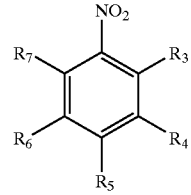

wherein $R_3$ through $R_7$ are independently selected from the group consisting of hydrogen, alkyl, aryl, acyl, hydroxyl, alkoxy, acyloxy, $NR_8(R_9)$, nitro, nitroso, halogen, and sulfonyl, or any two adjacent R's can form a cyclic ring that is aryl, cycloalkyl, polyaryl, or heterocyclic; and $R_8$ and $R_9$ are independently selected from the group consisting of hydrogen, alkyl, aryl, acyl, and nitroso. Preferably $R_8$ is hydrogen and $R_9$ is alkyl. Preferably, $R_3$ is hydroxyl, $R_6$ is nitro, and $R_4$ is alkyl.

The hydroxylamine compounds that can be employed in combination with the nitrosoanilines and quinone imine oximes in the practice of the present invention are preferably of the structure:

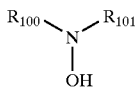

wherein $R_{100}$ and $R_{101}$ are independently selected from the group consisting of hydrogen, alkyl, alkylidene, benzylidene, aryl, benzyl, $COR_{102}$, $COOR_{102}$, $CONR_{102}R_{103}$, cyclic, heterocyclic, hydroxyalkyl, and substituted alkyl or aryl where the substituents are C, O, N, S, or P, or $R_{100}$ and $R_{101}$ can be taken together to form a ring structure of five to seven members.

The phenylenediamine compounds that can be employed in combination with the nitrosoanilines and quinone imine oximes in the practice of the present invention are preferably of the structure:

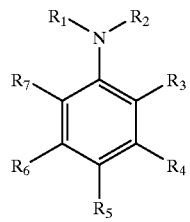

wherein $R_1$ and $R_2$ are independently selected from the group consisting of hydrogen, alkyl, aryl, acyl, hydroxyl, alkoxy, nitroso, and sulfonyl, or $R_1$ and $R_2$ can form a cyclic ring that is aryl, cycloalkyl, polyaryl, or heterocyclic;

$R_3$ through $R_7$ are independently selected from the group consisting of hydrogen, alkyl, aryl, acyl, hydroxyl, alkoxy, acyloxy, $NR_8(R_9)$, nitro, nitroso, halogen, and sulfonyl, or any two adjacent R's can form a cyclic ring that is aryl, cycloalkyl, polyaryl, or heterocyclic, provided that at least one of $R_3$ through $R_7$ must be an $NR_8(R_9)$ group; and $R_8$ and $R_9$ are independently selected from the group consisting of hydrogen, alkyl, aryl, acyl, and nitroso. Preferably, $R_1$ is hydrogen, $R_2$ is alkyl or aryl, $R_8$ is hydrogen, and $R_9$ is alkyl.

The quinone compounds that can be employed in combination with the nitrosoanilines and quinone imine oximes in the practice of the present invention are preferably of the structure:

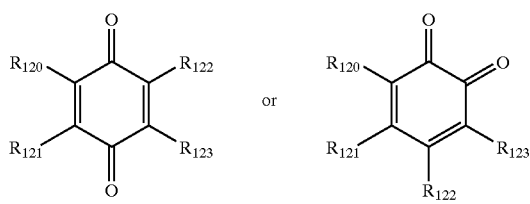

wherein $R_{120}$, $R_{121}$, $R_{122}$, and $R_{123}$ are independently selected from the group consisting of hydrogen, alkyl, aryl, cycloalkyl, sulfonyl, heterocyclic, substituted alkyl, substituted aryl, $OR_{110}$, $NR_{110}R_{111}$, $SR_{110}$, NO, $NO_2$, CN, $COR_{112}$, and halogen, or $R_{120}$ and $R_{121}$ can be taken together and/or $R_{122}$ and $R_{123}$ can be taken together to form one or two ring structures, respectively, either of which can be of five to seven members;

$R_{110}$ and $R_{111}$ are independently selected from the group consisting of hydrogen, alkyl, aryl, benzyl, cyclic, heterocyclic, substituted alkyl or aryl where the substituents are C, O, N, S, or P, and $COR_{102}$, or $R_{110}$ and $R_{111}$ can be taken together to form a ring structure of five to seven members;

$R_{112}$ is $R_{102}$, $OR_{102}$, or $NR_{102}R_{103}$; and $R_{102}$ and $R_{103}$ are independently selected from the group consisting of hydrogen, alkyl, aryl, benzyl, cyclic, heterocyclic, and substituted alkyl or aryl where the substituents are C, O, N, S, or P, or $R_{102}$ and $R_{103}$ can be taken together to form a ring structure of five to seven members.

The hydroquinone compounds that can be employed in combination with the nitrosoanilines and quinone imine oximes in the practice of the present invention are preferably of the structure:

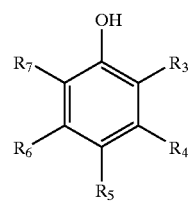

wherein $R_3$ through $R_7$ are independently selected from the group consisting of hydrogen, alkyl, aryl, acyl, hydroxyl, alkoxy, acyloxy, $NR_8(R_9)$, nitro, nitroso, halogen, and sulfonyl, or any two adjacent R's can form a cyclic ring that is aryl, cycloalkyl, polyaryl, or heterocyclic, provided that at least one of $R_3$ through $R_7$ must be an OH group; and $R_8$ and $R_9$ are independently selected from the group consisting of hydrogen, alkyl, aryl, acyl, and nitroso. Preferably, either $R_5$ is OH and $R_3$ and $R_6$ are alkyl or $R_3$ is OH and $R_5$ is alkyl.

In the foregoing, alkyl (or substituted alkyl) groups, or the alkyl moieties of alkoxy groups, preferably contain one to 15 carbon atoms, e.g., methyl, ethyl, propyl, butyl, pentyl, hexyl, heptyl, octyl, nonyl, decyl, undecyl, dodecyl, tridecyl, tetradecyl, pentadecyl, and the like, and isomers thereof, e.g., t-butyl, 2-ethylhexyl, and the like. It is more preferred that the alkyl (or substituted alkyl) groups be of one to five carbon atoms (e.g., methyl, ethyl, propyl, butyl, pentyl, and isomers thereof). Substituents on the substituted alkyl groups can be any moiety that will not interfere with the functions of the compounds. Aryl groups are preferably of from six to 10 carbon atoms, e.g., phenyl or naphthyl, which, in addition, may be substituted with noninterfering substituents, e.g., lower alkyl groups, halogens, and the like.

The effective amount of inhibitor(s) used in the practice of the present invention comprising the nitrosoaniline and/or quinone imine oxime compound(s), alone or in combination with a nitroxyl, and/or nitroaromatic, and/or quinone alkide, and/or quinone, and/or hydroquinone, and/or hydroxylamine, and/or phenylenediamine compound(s), is typically about 1 to 2,000 ppm, based on the weight of the ethylenically unsaturated monomer, although amounts outside this range may be appropriate depending upon the conditions of use. The amount is preferably in the range of from about 5 to about 1,000 ppm, based on the weight of the ethylenically unsaturated monomer.

The effective amount of air or oxygen used in the practice of the present invention is typically about 1 to 2,000 ppm, based on the weight of the ethylenically unsaturated monomer, although amounts outside this range may be appropriate depending upon the conditions of use. The amount is preferably in the range of from about 1 to about 1,000 ppm, based on the weight of the ethylenically unsaturated monomer.

Preferred embodiments of the instant invention comprise a process wherein a mixture is used that is from 1 to 99 percent by weight of at least one nitrosoaniline compound and 99 to 1 percent by weight of at least one additional compound. A more preferred mixture comprises from 5 to 75 percent by weight of at least one nitrosoaniline compound and 95 to 25 percent by weight of at least one additional compound. A still more preferred mixture comprises from 5 to 50 percent by weight of at least one nitrosoaniline compound and 95 to 50 percent by weight of at least one additional compound.

The ethylenically unsaturated monomer, the premature polymerization of which is an object of the present invention, can be any such monomer for which unintended polymerization during its manufacture, storage, and/or distribution is a problem. Among those monomers that will benefit from the practice of the present invention are: styrene, α-methylstyrene, styrene sulfonic acid, vinyltoluene, divinylbenzenes, polyvinylbenzenes, alkylated styrene, 2-vinylpyridine, acrylonitrile, methacrylonitrile, methyl acrylate, ethyl acrylate, methyl methacrylate, ethyl methacrylate, acrylic acid, methacrylic acid, butadiene, chloroprene, isoprene, and the like.

The ethylenically unsaturated monomers will not necessarily be stabilized indefinitely by the presence of the inhibitor blend, especially when the monomers are heated as in distillation, but they can be considered to be stabilized as long as there is a measurable increase in the time for which they can be heated before the onset of polymerization in a static system and/or the amount of polymer made at constant temperature remains constant over time in a dynamic system.

Those skilled in the art will understand that, if desired, additional free radical scavengers can be included in the stabilized compositions. For example, air or $O_2$, as disclosed in U.S. Pat. Nos. 5,545,782 and 5,545,786, can be added, as can the dihetero-substituted benzene compounds having at least one transferable hydrogen, e.g., a quinone derivative such as the mono-methyl-ether of hydroquinone disclosed in European Patent Application 0 765 856 A1, and other inhibitors well-known to those skilled in the art. The disclosures of the foregoing are incorporated herein by reference in their entirety.

The polymerization inhibitor composition can be introduced into the monomer to be protected by any conventional method. It can be added as a concentrated solution in suitable solvents just upstream from the point of desired application by any suitable means. For example, the individual inhibiting components can be injected separately or in combination to the monomer feed tank prior to injection into a distillation train. The individual inhibiting components can also be injected separately into the distillation train along with the incoming feed or through separate entry points, provided there is an efficient distribution of the inhibitors. Since the inhibitors are gradually depleted during the distillation operation, it is generally advantageous to maintain the appropriate amount of the inhibitor mixture in the distillation apparatus by adding inhibitors during the course of the distillation process. Adding inhibitors can be done either on a generally continuous basis or intermittently, in order to maintain the concentration of inhibitor mixture above the minimum required level.

The distillation method of the present invention is suitable for use in virtually any type of separation of a polymerizable ethylenically unsaturated monomer wherein the monomer is subjected to temperatures above room temperature. Thus, the process of the present invention has been found particularly useful in vacuum distillation techniques, the preferred method for separating unstable organic liquid mixtures. The amount of polymerization inhibitor added may vary over a wide range depending upon the conditions of distillation. Generally, the degree of stabilization is proportional to the amount of inhibitor added. In accordance with the present invention, it has been found that inhibitor concentrations generally between about 50 ppm and about 3000 ppm by weight have generally provided suitable results, depending primarily upon the temperature of the distillation mixture and the degree of inhibition desired. More often, however, with the inhibitor of the present invention it is used in concentrations of 100 to 1000 ppm.

During vacuum distillation of ethylenically unsaturated monomer, the temperature of the reboiler is preferably maintained from about 65° C. to about 130° C. by controlling reboiler pressure at from about 30 mm to about 400 mm of Hg. Under such conditions, in a distillation apparatus having a distillation zone containing from about 50 to about 100 distillation stages, inhibitor mixture concentrations of from about 100 ppm to about 2000 ppm by weight are suitable, whereas concentrations of from about 100 ppm to about 600 ppm by weight are preferably, 200 to 600 ppm by weight, in the case of styrene distillation and concentrations in the range of from about 200 ppm to about 1000 ppm by weight are preferred for distillation of divinylbenzene. The foregoing ranges are based upon distillation temperatures of from about 65° C. to about 150° C. and residence times of between about 2 and 4 hours. Obviously, in the lower portions of the temperature and residence time ranges, smaller amounts of inhibitor may be utilized. Obviously, amounts of inhibitor greater than those specified hereinabove may be employed, although the advantages of adding the additional inhibitor are not significant and are outweighed by the corresponding increase in cost.

The polymerization inhibitor of the present invention may be introduced into the distillation apparatus in any convenient manner which permits efficient distribution of the inhibitor throughout the apparatus. Typically and most advantageously, the required amount of inhibitor is simply added to the reboiler area of the distillation column, although equivalent results may be obtained by incorporating the inhibitor into the incoming hot stream of monomer. Also, the inhibitor may be added at both reboiler and directly into the distillation column. Either and/or both methods of addition provide a distribution of inhibitor which is commensurate with the distribution of monomer within the distillation system and is essential for effective polymerization inhibition.

It is generally necessary to maintain the appropriate amount of inhibitor in the distillation apparatus by adding inhibitor during the course of the distillation process, either on a generally continuous basis or on an intermittent basis. The means by which the maintenance of the necessary concentration of the inhibitor system is carried out is of no particular importance as long as the concentration of inhibitor is kept above or about the minimum required level.

One method by which the amount of inhibitor which is gradually depleted during distillation and the increased cost necessitated thereby may be minimized is by recycling a portion of the distillation residue or tar back into the distillation system. It has been found that the distillation residue contains a substantial quantity of polymerization inhibitor which may be re-utilized in the distillation system with a concomitant reduction in the process requirements for additional inhibitor. Moreover, by recycling a portion of the tar, the amount of inhibitor within the distillation system may be significantly increased, thereby enhancing protection against polymerization within the system.

The tar may be recycled back into the distillation system at any desirable point therein such as would be obvious to those skilled in the art. However, in a typical distillation train comprising a first fractionation column, a recycle column, and a finishing column, adequate inhibitor protection within the recycle column has been found to be essential to the elimination of thermal polymer, since the high distillation temperatures necessary to achieve adequate fractionation between the similar boiling compounds separated therein causes the formation of a substantial portion of the total thermal polymer formed within the distillation system as a whole. Indeed, with conventional processes, approximately 80% of the total thermal polymer formed is attributable to the recycle column. Accordingly, in the preferred embodiment, the portion of tar recycled is recycled to at least the recycle column, and preferably into the lower regions of the recycle column in order to provide a locus of inhibitor distribution which corresponds to the distribution of ethylenically unsaturated monomer therein. Optionally, additional tar may be recycled for addition back into the distillation system at other points, such as, for example, back into the first fractionation column.

One convenient method by which the tar may be recycled back into the distillation system is simply by incorporating the tar into an incoming feed of monomer or inhibitor. The amount of tar which is recycled back into the distillation system relative to the amount of feed may comprise any desirable amount. A larger amount of tar recycle will increase the loading of inhibitor within the distillation system. However, larger amounts of tar recycle will also increase the volume of bottoms material, and the amount of tar recycle will necessarily be constrained thereby.

The high purity overhead product withdrawn from the distillation apparatus will generally contain above about 97% and typically above about 99% by weight ethylenically unsaturated monomer, depending upon the ultimate use. The bottoms product may contain polymeric material, undistilled monomer and unspent inhibitor. This fraction is withdrawn from the distillation apparatus for further processing. In one particularly preferred embodiment of the present invention, a portion of the bottoms product, containing substantial amounts of re-useable inhibitor, is recycled for introduction into the distillation apparatus. The recycled portion of the bottoms product may be added to the distillation apparatus by any method known to those skilled in the art. Best results are obtained by adding the recycled portion at a location in the distillation apparatus which will yield a distribution of inhibitor which coincides with the distribution of monomer therein. By recycling the inhibitor-containing bottoms, the inhibitor may thus be reused, accruing thereby a significant reduction in the process requirements for inhibitor.

The advantages and the important features of the present invention will be more apparent from the following examples.

EXAMPLES

Procedure for Dynamic Reboiler Test with Feed Shut-Off

Preparation of Feed Solution.

T-Butylcatechol (TBC) is removed from commercially available styrene by distillation under vacuum. Removal of TBC is verified by caustic titration. The desired amount of inhibitor(s) is added to this TBC-free styrene either directly or by first making a concentrated solution of the inhibitor in TBC-free styrene followed by further dilution with TBC-free styrene.

Procedure for Reboiler Test under Ambient Conditions

A quantity of the Feed Solution containing inhibitor (blend) at the desired charge (stated as a wt/wt total inhibitor to styrene) is added to a round-bottom flask (the "Pot") and heated to the desired temperature (usually 116° C.) and brought to reflux by adjusting the pressure/vacuum. Once the Pot contents are at temperature, a continuous stream of fresh Feed Solution is begun at a rate that will add the volume of the initial Pot solution to the Pot over a period of time called the residence time (typically one hour). At the same time that the fresh Feed Solution flow is begun, the Bottoms Stream flow is also begun. The Bottoms Stream is solution in the Pot that is removed at the same rate as the fresh Feed Solution is added. The equal flows of Feed and Bottoms streams cause the quantity in the Pot to remain constant over the time of the experiment while allowing continuous replenishment of inhibitor. This procedure simulates the way inhibitors are used in a distillation train of a plant producing vinyl monomers. The experiment continues with flow in and out of the Pot for a specified period of time, typically seven hours. Samples are collected hourly from the Bottoms Stream. These samples are analyzed for polymer content via the methanol turbidity method. The amount of polymer in the samples is an indication of effectiveness of the inhibitor being tested. The lower the amount of polymer in the hourly samples, the more effective the inhibiting system should be during normal operation of a continuous manufacturing or purification process.

It should be noted that the methanol turbidity method for polymer analysis usually involves absorbance readings at 420 nm. We have found that some C-nitrosoanilines have absorbances that interfere with polymer analysis at this wavelength. Thus, in many instances, polymer was quantified at 600 nm instead of 420 nm.

Procedure for Reboiler Test with Air Injection

This procedure is the same as that under ambient conditions except that a gas sparging tube is inserted into the contents of the Pot. Air is injected through this sparging tube at a rate of 6 cc/min throughout the test.

Procedure for Reboiler Test with Argon Injection

This procedure is the same as that under ambient conditions except that argon gas is sparged through the Feed Solution and the apparatus at 6 cc/min for 15 minutes prior to heating the Pot. Throughout the remainder of the test, argon is injected into the contents of the Pot via a sparging tube at a rate of 6 cc/min while the Feed Solution is maintained under an argon blanket.

Procedure for Feed Shut-Off

At the end of the Reboiler Test Run (typically seven hours), a sample is collected from the Bottoms Stream. This sample corresponds to Feed Shut-Off Time=0 minutes. The flows of fresh Feed Solution and Bottoms Stream are stopped. The vacuum and temperature are monitored and adjusted to maintain boiling at the desired temperature of the experiment. If gas injection is being used, the injection of gas(es) is continued at the designated rate throughout feed shut-off. Samples are periodically removed from the Pot (typically every five minutes). These samples are analyzed for polymer content via the methanol turbidity method. A longer period of time before initiation of significant polymer formation is an indication of a more effective inhibiting system in the event of a loss of feed in the plant. Additionally, the lower the polymer number at a specific length of time after feed shut-off, the more effective the inhibitor system at providing protection for that length of time.

The results of experiments showing the improved inhibition provided by the present invention are shown in Tables 1 through 7. In these tables, the following abbreviations apply:

NA-1 is N-phenyl-4-nitrosoaniline

NA-2 is N-(1,4-dimethylpentyl)-4-nitrosoaniline

DNBP is 2,4-dinitro-6-sec-butylphenol

QM is 4-benzylidene-2,6-di-tert-butylcyclohexa-2,5-dienone nitroxyl is 4-oxo-TEMPO.

QIO is N-acetyloxy-N'-phenyl-1,4-diiminocyclohexa-2,5-diene.

DEHA is N,N-diethylhydroxylamine.

PDA is N-phenyl-N'-(1,4-dimethylpentyl)-paraphenylenediamine.

Naugard I-31 is a blend of PDA and DNBP.

Quinone is 2,5-di-tert-butyl-1,4-benzoquinone.

Hydroquinone is 2,5-di-tert-butyl-1,4-hydroquinone.

TABLE 1

Combinations of Nitrosoanilines with Quinonemethides
Polymer measurements taken at 420 nm;
runs made under ambient conditions

| | | | Weight Percent Polymer | |
|---|---|---|---|---|
| Example Number | Inhibitor System | Dosage (ppm) | At steady state | 40 min. after feed shut-off |
| 1 | QM | 250 | 1.09 | 1.52 |
| 2 | NA-2 | 250 | 0.033 | 4.35 |
| 3 | NA-2/QM | 100/150 | 0.002 | 0.51 |
| 4 | QM | 500 | 0.33 | 0.59 |
| 5 | NA-1 | 500 | 0.062 | 0.032 |
| 6 | NA-1/QM | 250/250 | 0.014 | 0.045 |

As can be seen from examples 2 and 5 of Table 1, the C-nitrosoanilines, NA-1 and NA-2, are very effective inhibitors at steady state. Examples 3 and 6 of Table 1 show that the combination of nitrosoaniline and quinonemethide gives the preferred combination of highly effective steady state performance along with excellent protection in case of loss of feed, giving a combined performance which is better than the performance obtained from either component by itself.

TABLE 2

Combinations of Nitrosoanilines with Nitroxyls
Polymer measurements taken at 420 nm;
runs made under ambient conditions

| | | | Weight Percent Polymer | |
|---|---|---|---|---|
| Example Number | Inhibitor System | Dosage (ppm) | At steady state | 40 min. after feed shut-off |
| 1 | nitroxyl | 150 | 0.005 | 1.8 |
| 2 | nitroxyl | 100 | 0.002 | 2.7 |
| 3 | nitroxyl | 75 | 0.003 | 2.9 |
| 4 | nitroxyl | 50 | 0.002 | 3.9 |
| 5 | NA-1 | 250 | 0.014 | 1.54 |
| 6 | NA-1/nitroxyl | 200/50 | 0.012 | 0.53 |
| 7 | QIO | 250 | 0.53 | 2.5 |

TABLE 2-continued

Combinations of Nitrosoanilines with Nitroxyls
Polymer measurements taken at 420 nm;
runs made under ambient conditions

| | | | Weight Percent Polymer | |
|---|---|---|---|---|
| Example Number | Inhibitor System | Dosage (ppm) | At steady state | 40 min. after feed shut-off |
| 8 | QIO/nitroxyl | 200/50 | 0.021 | 1.3 |
| 9 | NA-2/DNBP | 85/150 | 0.093 | 0.51 |
| 10 | nitroxyl/NA-2/DNBP | 8/75/150 | 0.065 | 0.51 |
| 11 | NA-2/DNBP | 75/200 | 0.049 | 0.37 |
| 12 | nitroxyl/NA-2/DNBP | 10/50/200 | 0.043 | 0.22 |
| 13 | NA-2/DNBP | 100/200 | 0.017 | 0.36 |
| 14 | nitroxyl/NA-2/DNBP | 10/75/200 | 0.013 | 0.26 |

Examples 1 to 4 of Table 2 indicate the effectiveness of nitroxyls as inhibitors. As stated previously, this quality of nitroxyls is well-known. However, we have found that a dosage of less than 50 ppm in this test provides insufficient protection, and the test becomes unstable and unsafe to run. Additionally, even at dosages of 100 ppm in this test, the protection in feed shut-off is minimal. Thus, addition of a small amount of nitroxyl (i.e., 50 ppm or less) in this test would not be expected to provide significant enhancement to feed shut-off performance. However, significant enhancement in feed shut-off performance is obtained when 50 ppm of nitroxyl is added to a C-nitrosoaniline (compare examples 5 and 6) or to a quinoneimineoxime derivative (compare examples 7 and 8). Furthermore, examples 9–14 show that addition of 10 ppm or less of nitroxyl to blends of C-nitrosoaniline and nitrophenol, where the total dose of the tri-blend is even less than the comparative dose of the C-nitrosoaniline and nitrophenol alone, provides better performance at steady state and equal or better performance in feed shut-off than obtained by the baseline blends of C-nitrosoaniline and nitrophenol alone.

TABLE 3

Combinations of Nitrosoanilines with Air
Polymer measurements taken at 420 nm

| | | | Weight Percent Polymer | |
|---|---|---|---|---|
| Example Number | Inhibitor System | Dosage (ppm) | At steady state | 40 min. after feed shut-off |
| 1 | NA-2; argon injection | 250 | 0.001 | 1.05 |
| 2 | NA-2; argon injection | 150 | 0.024 | 2.95 |
| 3 | NA-2; argon injection | 100 | 0.04 | 3.4 |
| 4 | NA-2; air injection | 250 | 0.002 | 0.008 |
| 5 | NA-2; air injection | 100 | 0.001 | 2.4 |
| 6 | NA-2; air injection | 50 | 0.002 | 1.9 |
| 7 | NA-2; air injection | 25 | 0.021 | 2.9 |

The examples in Table 3 show that C-nitrosoanilines are highly effective inhibitors under both aerobic (air injection) and anaerobic (argon injection) conditions. However, the performance of these C-nitrosoanilines in the presence of air is significantly improved in both steady state and feed shut-off conditions (compare example 3 with examples 5, 6, and 7). To our knowledge, this behavior of C-nitrosoanilines has not been previously reported.

TABLE 4

Combinations of Nitrosoanilines with Nitroaromatics

| | | | Weight Percent Polymer | |
|---|---|---|---|---|
| Example Number | Inhibitor System | Dosage (ppm) | At steady state | 40 min. after feed shut-off |
| Polymer analysis made at 420 nm, ambient conditions | | | | |
| 1 | DNBP | 250 | 0.43 | 0.90 |
| 2 | NA-2 | 250 | 0.033 | 4.35 |
| 3 | NA-2/DNBP | 125/125 | 0.011 | 0.82 |
| 4 | DNBP | 500 | 0.21 | 0.40 |
| 5 | NA-1 | 500 | 0.062 | 0.03 |
| 6 | NA-1/DNBP | 250/250 | 0.008 | 0.11 |
| Polymer analysis made at 600 nm | | | | 50 min. after feed shut-off |
| 7 | DNBP | 250 | 0.39 | 0.80 |
| 8 | NA-2; argon injection | 250 | 0.001 | 2.06 |
| 9 | NA-2; argon injection | 100 | 0.04 | 3.98 |
| 10 | NA-2/DNBP; argon injection | 100/150 | 0.007 | 0.65 |
| 11 | DNBP; air injection | 250 | 0.20 | 0.51 |
| 12 | NA-2; air injection | 250 | 0.002 | 0.48 |
| 13 | NA-2; air injection | 100 | 0.001 | 3.53 |
| 14 | NA-2; air injection | 50 | 0.002 | 3.2 |
| 15 | NA-2/DNBP; air injection | 100/150 | 0.001 | 0.24 |
| 16 | NA-2/DNBP; air injection | 50/150 | 0.001 | 0.24 |

The examples in Table 4 show that the combination of a C-nitrosoaniline and a nitroaromatic compound provide enhanced performance over either component alone under ambient (dissolved air only), anaerobic (argon injection), and aerobic (air injection) conditions.

Comparing Examples 1 through 3 and Examples 4 through 6 under ambient conditions, Examples 7 through 10 under anaerobic conditions, and Examples 11 through 16 under aerobic conditions, it is seen that combining a C-nitrosoaniline and a nitroaromatic compound gives the preferred combination of highly effective steady state performance along with excellent protection in case of loss of feed, which is better than the combined performance obtained from either component alone when run under the respective ambient, anaerobic, or aerobic conditions.

TABLE 5

Combinations of Nitrosoanilines with Hydroxylamines
Polymer measurements taken at 600 nm;
runs made under conditions indicated

| | | | Weight Percent Polymer | |
|---|---|---|---|---|
| Example Number | Inhibitor System | Dosage (ppm) | At steady state | 40 min. after feed shut-off |
| 1 | DEHA; argon injection | 250 | 1.3 | 3.00 |
| 2 | NA-2; argon injection | 250 | 0.001 | 2.06 |
| 3 | NA-2/DEHA; argon injection | 125/125 | 0.003 | 1.45 |
| 4 | DEHA; air injection | 250 | <0.001 | 0.005 |
| 5 | NA-2; air injection | 250 | 0.002 | 0.485 |
| 6 | NA-2/DEHA; air injection | 125/125 | 0.001 | 0.001 |

The examples in Table 5 indicate that the blend of a C-nitrosoaniline with a hydroxylamine provide equivalent or better performance than either component alone at the same total dosage in both steady state and feed shut-off tests under both anaerobic (argon injection; Examples 1–3) and aerobic (air injection; Examples 4–6) conditions.

TABLE 6

Combinations of Nitrosoanilines with Phenylenediamines
Polymer measurements taken at 600 nm;
runs made under air injection conditions

| | | | Weight Percent Polymer | |
|---|---|---|---|---|
| Example Number | Inhibitor System | Dosage (ppm) | At steady state | 40 min. after feed shut-off |
| 1 | Naugard I-31 | 500 | 0.024 | 0.16 |
| 2 | NA-2 | 50 | 0.002 | 1.9 |
| 3 | NA-2/Naugard I-31 | 50/375 | 0.002 | 0.14 |
| 4 | NA-2 | 25 | 0.021 | 2.9 |
| 5 | NA-2/Naugard I-31 | 25/450 | 0.009 | 0.11 |
| 6 | PDA | 250 | 0.006 | 2.6 |
| 7 | NA-2 | 250 | 0.002 | 0.008 |
| 8 | NA-2/PDA | 125/125 | 0.001 | 0.006 |

Examples 6–8 of Table 6 show that combination of a C-nitrosoaniline and a phenylenediamine provide better performance than either component alone at the same total dosage in both steady state and feed shut-off tests. Examples 1–5 of Table 6 show that addition of just a small amount of C-nitrosoaniline to a blend of nitroaromatic and phenylenediamine provides a tri-blend with the preferred combination of highly effective steady state performance along with excellent protection in case of loss of feed which the nitroaromatic/phenylenediamine blend could not provide alone, even at a higher total dosage.

TABLE 7

Combinations of Nitrosoanilines
with Quinones and Hydroquinones

| | | | Weight Percent Polymer | |
|---|---|---|---|---|
| Example Number | Inhibitor System | Dosage (ppm) | At steady state | 40 min. after feed shut-off |
| Polymer analysis made at 420 nm, ambient conditions | | | | |
| 1 | Quinone | 300 | 3.98 | 4.30 |
| 2 | NA-2 | 250 | 0.033 | 4.35 |
| 3 | NA-2/Quinone | 75/200 | 0.02 | 1.5 |
| Polymer analysis made at 600 nm | | | | |
| 4 | Hydroquinone | 300 | 2.77 | 6.60 |
| 5 | NA-2; argon injection | 100 | 0.040 | 3.40 |
| 6 | NA-2/Hydroquinone; argon injection | 75/175 | 0.083 | 2.49 |
| 7 | NA-2; air injection | 100 | 0.001 | 2.4 |
| 8 | NA-2/Hydroquinone; air injection | 75/175 | 0.002 | 0.41 |

In view of the many changes and modifications that can be made without departing from principles underlying the invention, reference should be made to the appended claims for an understanding of the scope of the protection to be afforded the invention.

What is claimed is:

1. A method for inhibiting the premature polymerization of ethylenically unsaturated monomers comprising adding to said monomers an effective amount of:
   A) at least one first inhibitor selected from the group consisting of C-nitrosoaniline compounds; and
   B) at least one second inhibitor selected from the group consisting of quinone alkides, nitroaromatic compounds, hydroxylamine compounds, phenylenediamine compounds, quinone compounds, and hydroquinone compounds.

2. The method of claim 1 wherein the first inhibitor is selected from the group consisting of C-nitrosoaniline compounds of the structure:

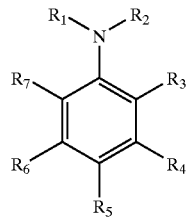

wherein:
R$_1$ and R$_2$ are independently selected from the group consisting of hydrogen, alkyl, aryl, acyl, hydroxyl, alkoxy, nitroso, and sulfonyl, or R$_1$ and R$_2$ can form a cyclic ring that is aryl, cycloalkyl, polyaryl, or heterocyclic;

R$_3$ through R$_7$ are independently selected from the group consisting of hydrogen, alkyl, aryl, acyl, hydroxyl, alkoxy, acyloxy, NR$_8$(R$_9$), nitro, nitroso, halogen, and sulfonyl, or any two adjacent R's can form a cyclic ring that is aryl, cycloalkyl, polyaryl, or heterocyclic, provided that at least one of R$_3$ through R$_7$ must be a nitroso group; and R$_8$ and R$_9$ are independently selected from the group consisting of hydrogen, alkyl, aryl, acyl, and nitroso.

3. The method of claim 2 wherein at least one of R$_1$ and R$_2$ is hydrogen.

4. The method of claim 2 wherein the C-nitrosoaniline compound is N-phenyl-4-nitrosoaniline.

5. The method of claim 2 wherein the C-nitrosoaniline compound is N-(1,4-dimethylpentyl)-4-nitrosoaniline.

6. The method of claim 1 wherein at least one second inhibitor is a nitroaromatic compound.

7. The method of claim 1 wherein at least one second inhibitor is a quinone methide compound.

8. The method of claim 1 wherein at least one second inhibitor is a quinone compound.

9. The method of claim 1 wherein at least one second inhibitor is a hydroquinone compound.

10. The method of claim 1 wherein at least one second inhibitor is a hydroxylamine compound.

11. The method of claim 1 wherein at least one second inhibitor is a phenylenediamine compound.

12. The method of claim 1 carried out in the presence of oxygen.

13. The method of claim 1 wherein the ethylenically unsaturated monomer is selected from the group consisting of styrene, α-methylstyrene, styrene sulfonic acid, vinyltoluene, divinylbenzenes, polyvinylbenzenes, alkylated styrene, 2-vinylpyridine, acrylonitrile, methacrylonitrile, methyl acrylate, ethyl acrylate, methyl methacrylate, ethyl methacrylate, acrylic acid, methacrylic acid, butadiene, chloroprene, and isoprene.

14. A composition of matter comprising:
A) an ethylenically unsaturated monomer;
B) an effective inhibiting amount, sufficient to prevent premature polymerization during distillation or purification of said ethylenically unsaturated monomer, of:
   i) at least one first inhibitor selected from the group consisting of C-nitrosoaniline compounds; and
   ii) at least one second inhibitor selected from the group consisting of quinone alkides, nitroaromatic compounds, hydroxylamine compounds, phenylenediamine compounds, quinone compounds, and hydroquinone compounds; and
C) oxygen or air in an amount effective to enhance the inhibiting activity of said first and second inhibitors.

15. The composition of claim 14 wherein the first inhibitor is selected from the group consisting of C-nitrosoaniline of the structure:

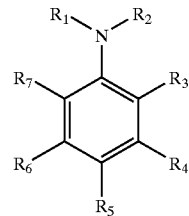

wherein
R$_1$ and R$_2$ are independently selected from the group consisting of hydrogen, alkyl, aryl, acyl, hydroxyl, alkoxy, nitroso, and sulfonyl, or R$_1$ and R$_2$ can form a cyclic ring that is aryl, cycloalkyl, polyaryl, or heterocyclic;

R$_3$ through R$_7$ are independently selected from the group consisting of hydrogen, alkyl, aryl, acyl, hydroxyl, alkoxy, acyloxy, NR$_8$(R$_9$), nitro, nitroso, halogen, and sulfonyl, or any two adjacent R's can form a cyclic ring that is aryl, cycloalkyl, polyaryl, or heterocyclic, provided that at least one of R$_3$ through R$_7$ must be a nitroso group; and R$_8$ and R$_9$ are independently selected from the group consisting of hydrogen, alkyl, aryl, acyl, and nitroso.

16. The composition of claim 15 wherein at least one of R$_1$ and R$_2$ is hydrogen.

17. The method of claim 14 wherein the ethylenically unsaturated monomer is selected from the group consisting of styrene, α-methylstyrene, styrene sulfonic acid, vinyltoluene, divinylbenzenes, polyvinylbenzenes, alkylated styrene, 2-vinylpyridine, acrylonitrile, methacrylonitrile, methyl acrylate, ethyl acrylate, methyl methacrylate, ethyl methacrylate, acrylic acid, methacrylic acid, butadiene, chloroprene, and isoprene.

18. The composition of claim 14 wherein at least one second inhibitor is a nitroaromatic compound.

19. The composition of claim 14 wherein at least one second inhibitor is a quinone methide compound.

20. The composition of claim 14 wherein at least one second inhibitor is a quinone compound.

21. The composition of claim 14 wherein at least one second inhibitor is a hydroquinone compound.

22. The composition of claim 14 wherein at least one second inhibitor is a hydroxylamine compound.

23. The composition of claim 14 wherein at least one second inhibitor is a phenylenediamine compound.

24. A method for distilling a feed comprising at least one polymerizable ethylenically unsaturated monomer, said method comprising the steps of:
A) introducing a feed comprising at least one polymerizable ethylenically unsaturated monomer into a distillation apparatus;
B) introducing a polymerization inhibiting effective amount of:
   i) at least one first inhibitor selected from the group consisting of C-nitrosoaniline compounds:

ii) at least one second inhibitor selected from the group consisting of quinone alkides, nitroaromatic compounds, hydroxylamine compounds, phenylenediamine compounds, quinone compounds, and hydroquinone compounds into said distillation apparatus; and C) distilling said feed under distillation conditions in the presence of said inhibitors to recover from said distillation apparatus an overhead product of high purity ethylenically unsaturated monomer and a residual bottoms fraction having a reduced content of polymeric material.

25. The method claim 24 further comprising recycling a portion of said bottoms fraction back into said distillation apparatus.

26. The method of claim 25 carried out in the presence of oxygen.

27. The method of claim 25 wherein the first inhibitor is selected from the group consisting of C-nitrosoaniline compounds of the structure:

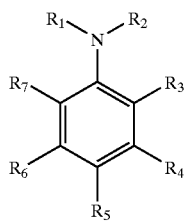

wherein
  $R_1$ and $R_2$ are independently selected from the group consisting of hydrogen, alkyl, aryl, acyl, hydroxyl, alkoxy, nitroso, and sulfonyl, or $R_1$ and $R_2$ can form a cyclic ring that is aryl, cycloalkyl, polyaryl, or heterocyclic;
  $R_3$ through $R_7$ are independently selected from the group consisting of hydrogen, alkyl, aryl, acyl, hydroxyl, alkoxy, acyloxy, $NR_8(R_9)$, nitro, nitroso, halogen, and sulfonyl, or any two adjacent R's can form a cyclic ring that is aryl, cycloalkyl, polyaryl, or heterocyclic, provided that at least one of $R_3$ through $R_7$ must be a nitroso group; and
  $R_8$ and $R_9$ are independently selected from the group consisting of hydrogen, alkyl, aryl, acyl, and nitroso.

28. The method of claim 24 carried out in the presence of oxygen.

29. The method of claim 24 wherein the first inhibitor is selected from the group consisting of C-nitrosoaniline compounds of the structure:

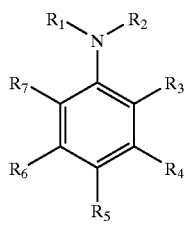

wherein
  $R_1$ and $R_2$ are independently selected from the group consisting of hydrogen, alkyl, aryl, acyl, hydroxyl, alkoxy, nitroso, and sulfonyl, or $R_1$ and $R_2$ can form a cyclic ring that is aryl, cycloalkyl, polyaryl, or heterocyclic;
  $R_3$ through $R_7$ are independently selected from the group consisting of hydrogen, alkyl, aryl, acyl, hydroxyl, alkoxy, acyloxy, $NR_8(R_9)$, nitro, nitroso, halogen, and sulfonyl, or any two adjacent R's can form a cyclic ring that is aryl, cycloalkyl, polyaryl, or heterocyclic, provided that at least one of $R_3$ through $R_7$ must be a nitroso group; and
  $R_8$ and $R_9$ are independently selected from the group consisting of hydrogen, alkyl, aryl, acyl, and nitroso.

30. The method of claim 29 wherein at least one of $R_1$ and $R_2$ is hydrogen.

31. The method of claim 24 wherein the ethylenically unsaturated monomer is selected from the group consisting of styrene, α-methylstyrene, styrene sulfonic acid, vinyltoluene, divinylbenzenes, polyvinylbenzenes, alkylated styrene, 2-vinylpyridine, acrylonitrile, methacrylonitrile, methyl acrylate, ethyl acrylate, methyl methacrylate, ethyl methacrylate, acrylic acid, methacrylic acid, butadiene, chloroprene, and isoprene.

32. The method of claim 24 wherein at least one second inhibitor is a nitroaromatic compound.

33. The method of claim 24 wherein at least one second inhibitor is a quinone methide compound.

34. The method of claim 24 wherein at least one second inhibitor is a quinone compound.

35. The method of claim 24 wherein at least one second inhibitor is a hydroquinone compound.

36. The method of claim 24 wherein at least one second inhibitor is a hydroxylamine compound.

37. The method of claim 24 wherein at least one second inhibitor is a phenylenediamine compound.

38. A composition of matter comprising
  A) at least one member selected from the group consisting of C-nitrosoaniline compounds; and
  B) at least one member selected from the group consisting of quinone alkides, nitroaromatic compounds, hydroxylamine compounds, phenylenediamine compounds, quinone compounds, and hydroquinone compounds.

39. The composition of claim 38 wherein the C-nitrosoaniline compounds are of the structure:

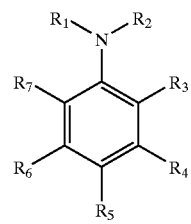

wherein
  $R_1$ and $R_2$ are independently selected from the group consisting of hydrogen, alkyl, aryl, acyl, hydroxyl, alkoxy, nitroso, and sulfonyl, or $R_1$ and $R_2$ can form a cyclic ring that is aryl, cycloalkyl, polyaryl, or heterocyclic;
  $R_3$ through $R_7$ are independently selected from the group consisting of hydrogen, alkyl, aryl, acyl, hydroxyl, alkoxy, acyloxy, $NR_8(R_9)$, nitro, nitroso, halogen, and sulfonyl, or any two adjacent R's can form a cyclic ring that is aryl, cycloalkyl, polyaryl, or heterocyclic, provided that at least one of $R_3$ through $R_7$ must be a nitroso group; and
  $R_8$ and $R_9$ are independently selected from the group consisting of hydrogen, alkyl, aryl, acyl, and nitroso.

40. The composition of claim 39 wherein at least one of $R_1$ and $R_2$ is hydrogen.

41. The composition of claim 38 further comprising at least one polymerizable ethylenically unsaturated monomer.

42. The method of claim 41 wherein the ethylenically unsaturated monomer is selected from the group consisting of styrene, α-methylstyrene, styrene sulfonic acid, vinyltoluene, divinylbenzenes, polyvinylbenzenes, alkylated styrene, 2-vinylpyridine, acrylonitrile, methacrylonitrile, methyl acrylate, ethyl acrylate, methyl methacrylate, ethyl methacrylate, acrylic acid, methacrylic acid, butadiene, chloroprene, and isoprene.

43. The composition of claim 38 wherein at least one second inhibitor is a nitroaromatic compound.

44. The composition of claim 38 wherein at least one second inhibitor is a quinone methide compound.

45. The composition of claim 38 wherein at least one second inhibitor is a quinone compound.

46. The composition of claim 38 wherein at least one second inhibitor is a hydroquinone compound.

47. The composition of claim 38 wherein at least one second inhibitor is a hydroxylamine compound.

48. The composition of claim 38 wherein at least one second inhibitor is a phenylenediamine compound.

* * * * *